(12) United States Patent  
Bagamery et al.

(10) Patent No.: US 9,737,274 B2  
(45) Date of Patent: Aug. 22, 2017

(54) TOMOGRAPHIC APPARATUS

(71) Applicant: Mediso Orvosi Berendezes Fejleszto es Szerviz Kft., Budapest (HU)

(72) Inventors: Istvan Bagamery, Budapest (HU); Zoltan Nyitrai, Budapest (HU)

(73) Assignee: Mediso Orvosi Berendezes Fejleszto es Szerviz Kft., Budapest (HU)

( * ) Notice: Subject to any disclaimer, the term of this patent is extended or adjusted under 35 U.S.C. 154(b) by 0 days.

(21) Appl. No.: 15/105,652

(22) PCT Filed: Dec. 17, 2013

(86) PCT No.: PCT/HU2013/000126  
§ 371 (c)(1),  
(2) Date: Jun. 17, 2016

(87) PCT Pub. No.: WO2015/092450  
PCT Pub. Date: Jun. 25, 2015

(65) Prior Publication Data  
US 2016/0331333 A1 Nov. 17, 2016

(51) Int. Cl.  
*G01T 1/24* (2006.01)  
*A61B 6/00* (2006.01)  
(Continued)

(52) U.S. Cl.  
CPC .......... *A61B 6/4417* (2013.01); *A61B 5/0042* (2013.01); *A61B 5/055* (2013.01);  
(Continued)

(58) Field of Classification Search  
CPC ..... G01T 1/249; G01T 1/1603; G01T 1/1611; G01T 1/2985; G06T 2207/10104;  
(Continued)

(56) References Cited

U.S. PATENT DOCUMENTS 6,965,661 B2 * 11/2005 Kojima .................. A61B 6/037  
                                                              378/10  
7,745,794 B2 6/2010 Schmidt  
(Continued)

FOREIGN PATENT DOCUMENTS

WO 2013160781 10/2013

OTHER PUBLICATIONS

European Patent Office,Notification of Transmittal (Form PCT/ISA/220, 1 pg.), International Search Report (Form PCT/ISA/210, 3 pgs.) and Written Opinion of the International Searching Authority (Form PCT/ISA/237, 4 pgs.), Jul. 16, 2014.

*Primary Examiner* — Kiho Kim  
(74) *Attorney, Agent, or Firm* — Wood Herron & Evans LLP

(57) ABSTRACT

The invention is a tomographic apparatus, in particular for examining a brain or a limb of a human and/or a primate animal, the apparatus (10) comprising an examination space (16) adapted for receiving a subject of a tomographic examination, and a PET ring (12) and a second imaging arrangement, being arranged around the examination space (16) in a substantially coaxial manner. The tomographic apparatus according to the invention comprises a PET ring (12) being displaceable between a PET operational state and a PET non-operational state, and comprises a second imaging arrangement adapted for being brought from a second imaging non-operational state to a second imaging operational state in the PET non-operational state of the PET ring (12).

3 Claims, 7 Drawing Sheets

(51) Int. Cl.
*A61B 6/03* (2006.01)
*A61B 5/00* (2006.01)
*A61B 5/055* (2006.01)

(52) U.S. Cl.
CPC .............. *A61B 6/032* (2013.01); *A61B 6/037* (2013.01); *A61B 6/4452* (2013.01); *A61B 6/501* (2013.01); *A61B 6/508* (2013.01)

(58) Field of Classification Search
CPC . G06T 2207/10088; G06T 2207/10081; G06T 2207/10108
See application file for complete search history.

(56) References Cited

U.S. PATENT DOCUMENTS

| | | | | |
|---|---|---|---|---|
| 2003/0058984 A1* | 3/2003 | Susami | ................ | A61B 6/4417 378/19 |
| 2003/0108147 A1* | 6/2003 | Kojima | ................ | A61B 6/4241 378/19 |
| 2003/0153828 A1* | 8/2003 | Kojima | ................ | A61B 6/032 600/425 |
| 2003/0233039 A1* | 12/2003 | Shao | ................ | G06T 7/0038 600/407 |
| 2004/0264626 A1* | 12/2004 | Besson | ................ | A61B 6/508 378/4 |
| 2005/0207530 A1* | 9/2005 | Inoue | ................ | A61B 6/032 378/63 |
| 2008/0001089 A1* | 1/2008 | Lusser | ................ | G01T 1/249 250/363.02 |
| 2008/0048124 A1* | 2/2008 | Pang | ................ | A61B 6/482 250/363.04 |
| 2009/0213983 A1* | 8/2009 | Vaquero Lopez | ..... | A61B 6/032 378/4 |
| 2010/0290584 A1 | 11/2010 | Vesel et al. | | |
| 2011/0019895 A1* | 1/2011 | Mizuta | ................ | G01T 1/1603 382/131 |
| 2011/0024636 A1* | 2/2011 | Gagnon | ................ | G01T 1/2985 250/362 |
| 2013/0151800 A1* | 6/2013 | Teshigawara | ......... | G01T 1/1611 711/159 |
| 2013/0204113 A1 | 8/2013 | Carmi | | |
| 2014/0066755 A1* | 3/2014 | Matteo | ................ | A61B 6/032 600/427 |
| 2014/0249408 A1* | 9/2014 | Collins | ................ | A61B 6/032 600/427 |

* cited by examiner

TOMOGRAPHIC APPARATUS

This application claims priority, under Section 371 and/or as a continuation under Section 120, to PCT Application No. PCT/HU2013/000126, filed on Dec. 17, 2013.

TECHNICAL FIELD

The invention relates to a tomographic apparatus comprising a PET (positron emission tomography) ring and a second imaging arrangement, preferably a CT (computed tomography) arrangement having a radiation source and a detector corresponding to the radiation source, or an MRI (magnetic resonance imaging) arrangement.

BACKGROUND ART

In recent years, the combination consisting of a positron emission tomograph and a conventional computed tomograph (for instance, x-ray tomograph) has become an accepted and widely applied imaging solution in the field of medical imaging diagnostics. The functional PET images and the higher-resolution CT images together provide valuable diagnostic information. Images provided by the PET arrangement may be advantageously combined also with MRI images.

In early solutions the separate PET and CT apparatuses adapted for examining human subjects were first combined, and were later accommodated in a common housing. Such apparatuses are disclosed for instance in US 2011/0224534 A1, US 2011/0077511 A1, US 2012/0046544 A1, US 2012/0085912 A1, and US 2012/0271164 A1. In the case of these apparatuses, the diameter of the bore or examination space adapted for receiving the patient is typically 600-800 mm, which makes these apparatuses suitable for performing whole-body scans. These scanners are thus suitable also for brain scans, but their resolution is limited due to the large diameter of the examination space.

For the above reasons, different types of apparatuses have been developed for examining small animals. In these apparatuses PET scanner rings of smaller diameter are applied, and the imaging field of the applied CT scanners is also much smaller. Such apparatuses are primarily suited for examining mice and rats, and have a bore size far smaller (60-110 mm) than the above introduced apparatuses. Accordingly, their resolution is on an order of magnitude better than the resolution of apparatuses adapted for performing human whole-body scans. Such an apparatus is disclosed for instance in the document with publication number WO 2012/171029 A1. In the apparatus according to the document, a specimen stage is rotated relative to the PET and CT scanners.

Other than combined PET/CT whole-body scanners, there are only a few prior art devices capable of examining the brain, skull or limbs of human or primate animals by combined PET and CT scanning. Such a solution is for instance the so-called NeuroPET-CT device, wherein the PET scanner ring is disposed behind the CT scanner. Because of the fairly large longitudinal size of the CT arrangement, the PET scanner ring has a considerably large blind area.

A portable PET detector capable of performing PET brain scans is presented in WO 2010/033159 A1. In addition to apparatus with such helmet-like detectors, a mobile apparatus comprising a foldable detector is also known, as described in US 2012/068076 A1. A similar apparatus is disclosed in U.S. Pat. No. 5,420,427. An apparatus capable of performing brain scans applying a PET scanner ring mounted on a movable gantry is described in US 2011/127434 A1.

Similarly aimed solutions for performing only CT scans are also known, e.g. from WO 2011/135185 A1, WO 2011/135186 A1, WO 2011/135187A1, and WO 2011/135191 A1. A similar concept is spelled out in US 2006/067464 A1.

Further PET-CT scanners, capable basically of performing whole-body scans, are described in US 2012/0265050 A1, U.S. Pat. No. 6,670,614 B1 and U.S. Pat. No. 8,351,566 B2. These apparatuses have the common disadvantage that the components adapted for taking the PET and CT images are arranged along the same circumferential region of the examination space such that they have overlapping fields of vision, which means that the PET components are arranged along a first portion of the circumference of a given slice of the examination space, the CT components being arranged along a second portion thereof. Therefore, there are configuration limitations for the PET and CT units in case of these solutions: for instance in certain solutions the PET detector cannot be ring-shaped because the PET detector units can only be arranged in a given region of the circumference.

In WO 2012/066469 A1 a detector is described that is capable of detecting particles generated during both PET and CT scans. In US 2012/0161014 A1 an arrangement is disclosed wherein the PET scanner arrangement comprises a plurality of PET rings, with CT apparatuses being disposed between neighbouring PET rings. A combined PET-CT apparatus is disclosed in DE 10 2007 061 596 A1.

U.S. Pat. No. 8,232,527 B2 discloses a PET apparatus comprising a secondary radiation source disposed in the examination space, the PET scanner ring being thus capable of detecting the radiation of the secondary radiation source in addition to radiation coming from the examination subject.

A combined PET-CT scanner apparatus adapted for taking whole-body scans is described in U.S. Pat. No. 7,652,256 B2. The scanner comprises a conventional CT apparatus, with a PET scanner insert extending to a small extent into the examination space of the CT scanner being incorporated in the apparatus. In U.S. Pat. No. 7,053,376 B2 a combined PET-CT scanner apparatus adapted for performing whole-body scans is described wherein a CT radiation source extends into the PET scanner ring. In U.S. Pat. No. 7,053,376 B2 such embodiments are also described wherein the PET scanner ring is arranged in a way similar to what is disclosed in US 2012/0161014 A1.

The prior art also comprises combined PET-MRI apparatuses.

In light of known solutions the need has arisen for a combined tomographic apparatus that comprises a PET arrangement and a second imaging arrangement—preferably a CT arrangement or MRI arrangement—, and is particularly adapted for examining the brain or a limb of a human and/or primate animal, and therefore the PET ring can preferably be dimensioned accordingly, and which apparatus allows performing a PET scan and a second imaging examination in a more advantageous manner than the known solutions, in such a way that the examination subject either does not need to move during the examinations, or needs to move only to a small extent and in a controlled way.

DESCRIPTION OF THE INVENTION

The primary object of the invention is to provide a tomographic apparatus which is free of the disadvantages of prior art solutions to the greatest possible extent.

A further object of the invention is to provide a combined tomographic apparatus that comprises a PET arrangement and a second imaging arrangement—preferably a CT arrangement or MRI arrangement, and is particularly adapted for examining the brain or a limb of a human and/or primate animal, i.e. the PET ring can preferably be dimensioned accordingly, and which apparatus allows performing a PET examination and a second imaging examination in a more advantageous manner than the known solutions such that the subject of the examination does not need to move between the two examinations.

The objects of the invention can be achieved by the tomographic apparatus according to claim 1. Preferred embodiments of the invention are defined in the dependent claims.

BRIEF DESCRIPTION OF THE DRAWINGS

Preferred embodiments of the invention are described below by way of example with reference to the following drawings, where.

MODES FOR CARRYING OUT THE INVENTION

Figure 1:
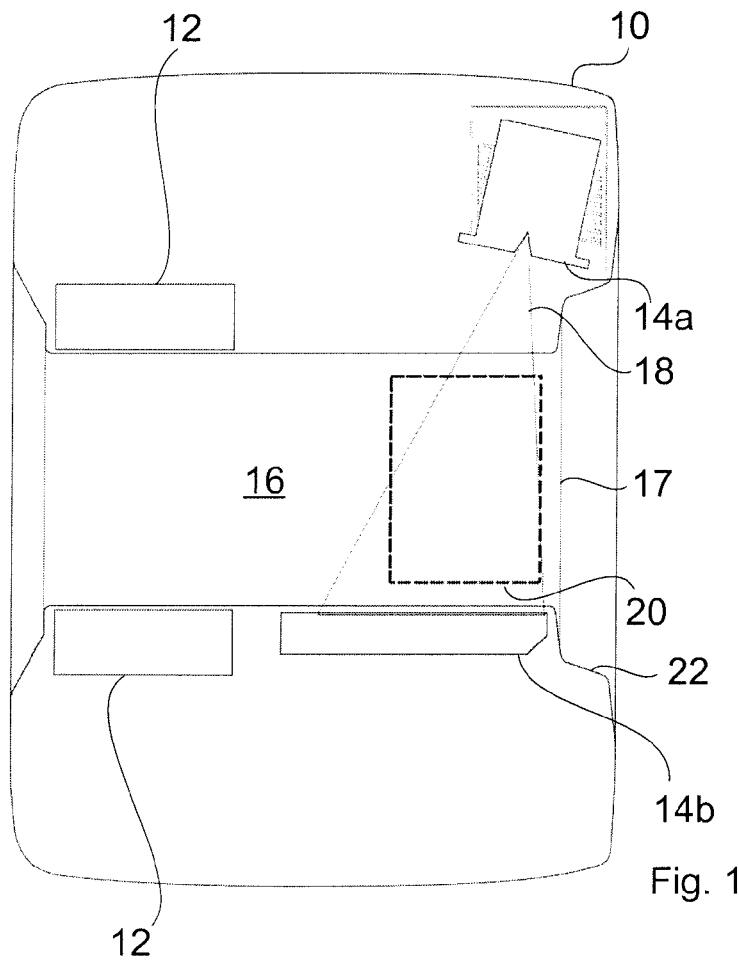
FIG. 1 illustrates an embodiment of the tomographic apparatus according to the invention, showing a schematic sectional view taken in the non-operational state of the PET ring and in the operational state of the CT arrangement that constitutes the second imaging arrangement.

The tomographic apparatus according to the invention is in particular adapted for examining a brain or a limb of a human and/or primate animal. In FIG. 1 a schematic sectional view of an embodiment of the apparatus according to the invention is shown. The tomographic apparatus 10 according to the invention comprises an examination space 16 adapted for receiving the subject of the tomographic examination, a PET ring 12, and a second imaging arrangement. The PET ring 12 and the second imaging arrangement are arranged in a substantially coaxial manner around the examination space 16.

Figure 3:
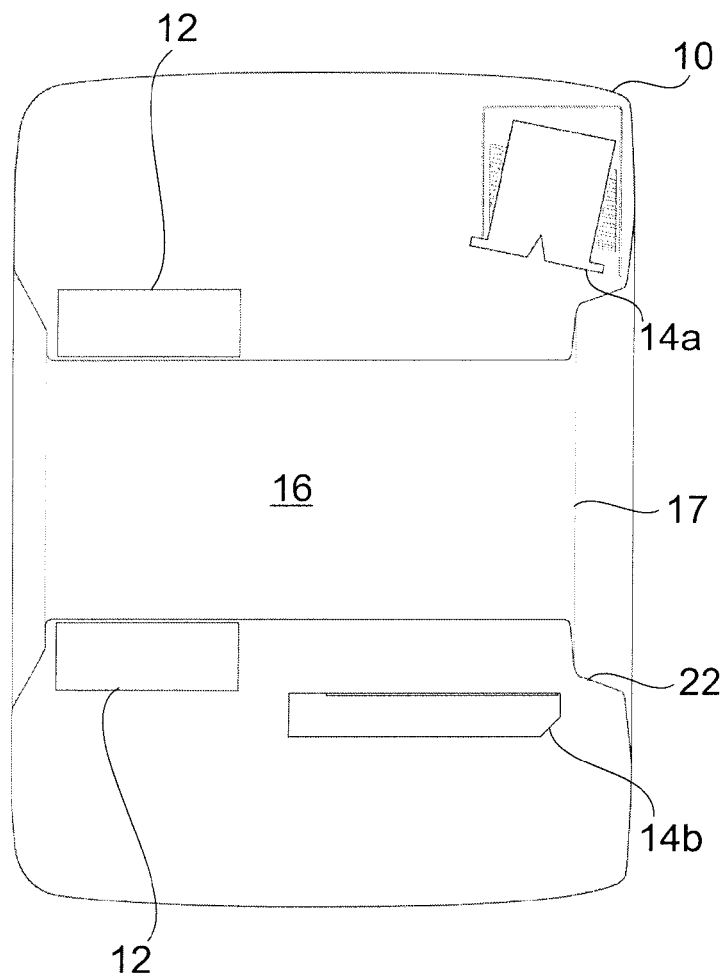
FIG. 3 shows the embodiment illustrated in FIG. 1 in a non-operational state of the PET ring and a non-operational state of the CT arrangement.
Figure 5:
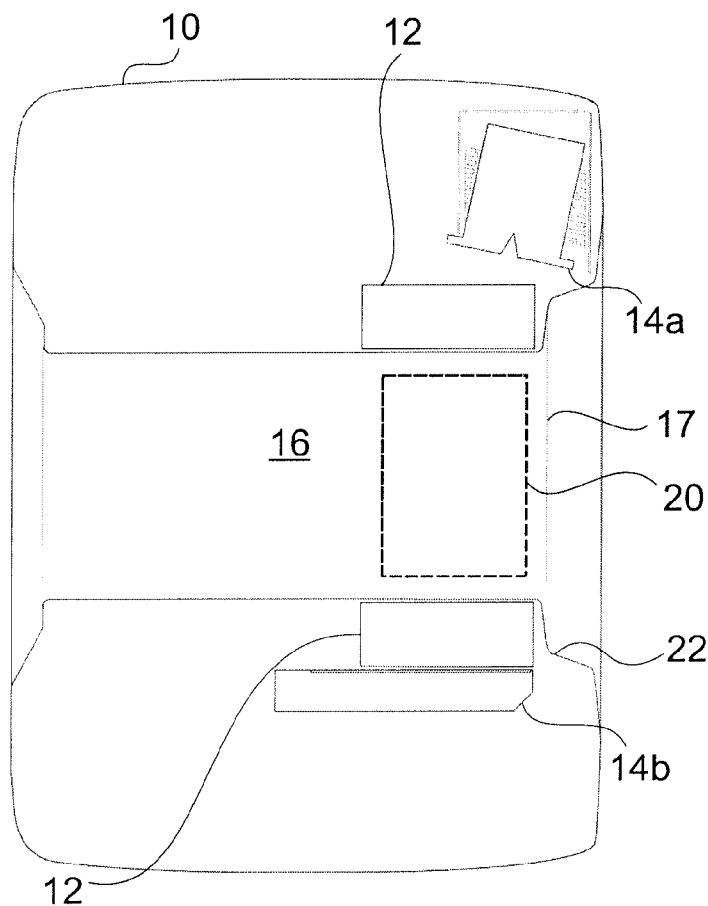
FIG. 5 shows the embodiment illustrated in FIG. 1 in an operational state of the PET ring and in a non-operational state of the CT arrangement.

In this embodiment the second imaging arrangement is a CT arrangement comprising a radiation source 14a and a detector 14b corresponding to the radiation source 14a. The radiation source is characteristically adapted for emitting typically X-ray radiation. In other embodiments the second imaging arrangement is an MRI arrangement. In the following, the relative arrangement of the PET ring and the second imaging arrangement is presented with applying a CT arrangement as the second imaging apparatus. Some advantageous features that are to be detailed below—related to the radiation source and the detector of the CT arrangement—only occur in case a CT arrangement is applied. The embodiments described herein can be modified such that the second imaging arrangement is an MRI arrangement. As FIGS. 1, 3, and 5 are sectional views, each drawing shows two rectangular sections of the PET ring 12.

The tomographic apparatus according to the invention comprises a PET ring 12 displaceable between a PET operational state and a PET non-operational state, and a second imaging arrangement adapted for being brought from a second imaging non-operational state to a second imaging operational state in the PET non-operational state of the PET ring 12. According to what was presented above, considering that a CT arrangement is applied as a second imaging arrangement, in the description of the embodiments terms "CT operational state" and "CT non-operational state", are used instead of the terms "second imaging operational state", and "second imaging non-operational state", respectively.

In the embodiment shown in FIG. 1 the examination space 16 is broadened at an inlet 17 thereof. This broadening is advantageous for anatomical reasons, because without it the widening shape of the neck, as well as the shape of the junction between the neck and the body could prevent the head from being inserted into the examination space 16 to the desired extent.

In the sectional view of FIG. 1 the PET ring of the apparatus according to the invention is in a PET non-operational state, that is, the PET ring is removed from the inlet 17 of the examination space 16 by displacing it around the examination space 16 inside the apparatus 10. At the same time, the CT arrangement is shown in FIG. 1 in a CT operational state, and therefore the examined subject—his body extending through the inlet 17—falls into an imaging field 20 of the CT arrangement.

It is shown in FIG. 1, that in this embodiment the radiation source 14a is arranged such that a side—facing the inlet 17 of the examination space 16—of the space part 18 irradiated by the radiation source 14a is aligned substantially parallel with the inlet 17. The more parallel the alignment of this side of the irradiated space part, the more even sampling of the imaging field 20 portions located close to the inlet 17 can be achieved. In the manner shown in FIG. 1, a broadening 22 allows the radiation source 14a to be tilted, as the arrangement of the broadening 22 forms a hollow portion in the apparatus 10 for receiving the shoulders.

Figure 2:
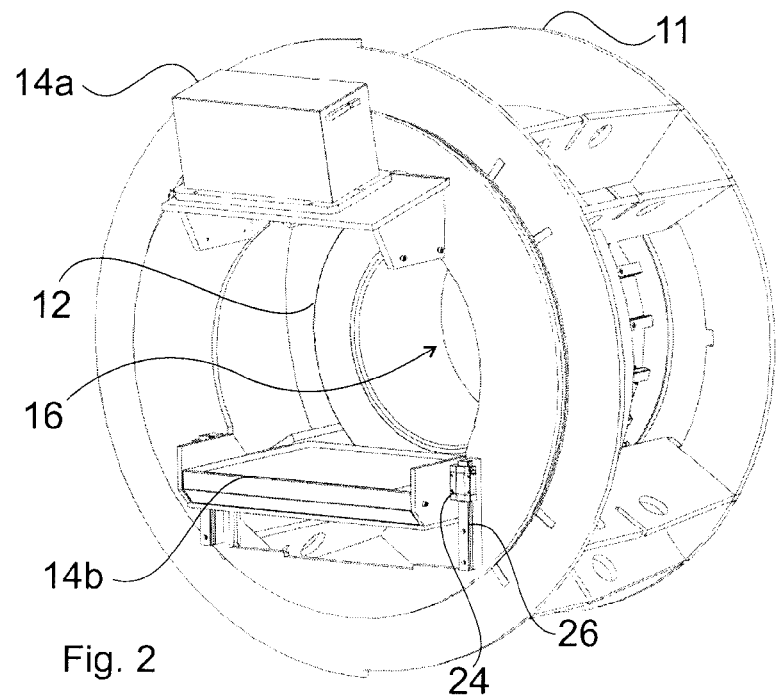
FIG. 2 is a spatial view of the state shown in FIG. 1.

In FIG. 2 the embodiment depicted in FIG. 1 is shown in a spatial drawing showing a more detailed view, that is, in FIG. 2 a CT operational state of the CT arrangement, as well as a PET non-operational state of the PET ring are shown. FIG. 2 shows the apparatus 10 with its cover removed, illustrating that the components of the CT arrangement—the radiation source 14a and the detector 14b—are attached to an intermediate ring. A retainer ring 11 is also shown in the figure, the position of the PET ring 12 inside the apparatus being determined by the distance ring, the retainer ring 11, and the ribs that connect them. As it is illustrated in drawings to be described below, the PET ring 12 may be displaced inside the structure constituted by the distance ring, the retainer ring 11, and the ribs.

It is shown in FIG. 2 that the detector 14b is connected to a rail 26 by means of a sliding connector 24 (trolley). The sliding connector 24 can be slid along the rail 26.

Figure 6:
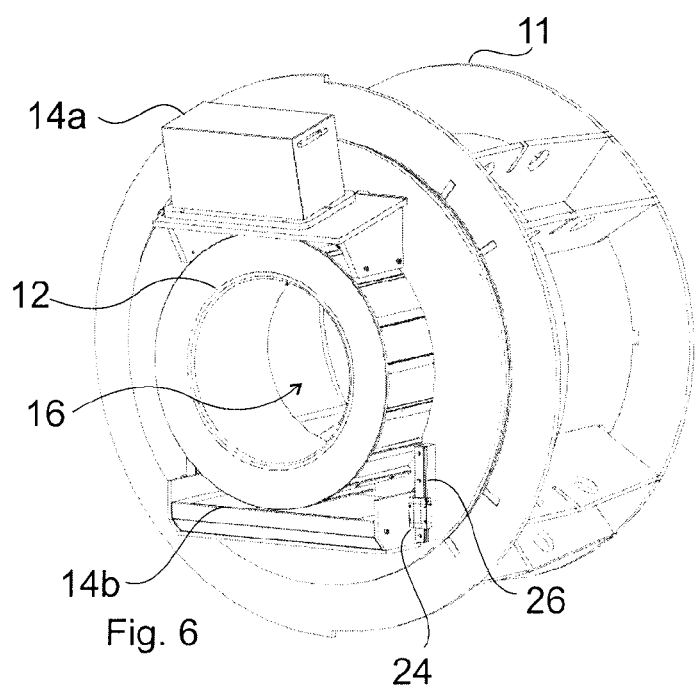
FIG. 6 illustrates the state of FIG. 5 in a spatial view.

FIG. 3 shows the apparatus 10 with the PET ring 12 in the PET non-operational state, and the CT arrangement in the CT non-operational state. In this embodiment the detector is pulled slightly backward from the examination space 16 in the CT non-operational state. Therefore, according to this embodiment, in the CT operational state the detector 14b is displaced toward the radiation source 14a with respect to the position it has in the CT non-operational state. In this embodiment the detector 14b has to be pulled backwards in order to allow the PET ring 12 to be inserted (fitted) between the radiation source 14a and detector 14b of the CT arrangement as shown in FIGS. 5 and 6.

Figure 4:
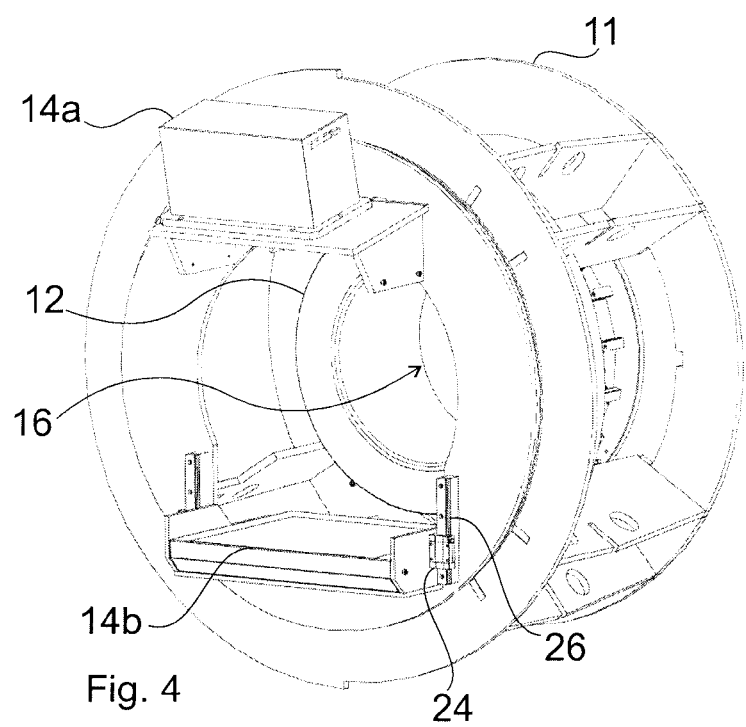
FIG. 4 illustrates the state of FIG. 3 in a spatial view.

In other embodiments the detector may be originally arranged to allow the PET ring to be slid between the components of the CT arrangement, however, it is preferable to arrange the detector as close to the radiation source as possible for the best quality CT images. It is therefore expedient to arrange the detector in the manner exemplified in FIGS. 1-6; such that the detector may be displaceable between the CT operational state and the CT non-operational state in the radial direction of the examination space 16. It is shown in FIG. 4 that in the CT non-operational state the detector 14b is slid along rail 26 to a lower, radially more outward position.

FIG. 5 illustrates the PET operational state of the embodiment shown in FIG. 1, wherein the PET ring 12 is moved into between the radiation source 14a and detector 14b of the CT arrangement (a state shown in FIGS. 5 and 6), while in the PET non-operational state it is moved out from between the radiation source 14a and detector 14b of the CT arrangement (a state shown in FIGS. 1 and 2). In the PET operational state the CT arrangement is in the CT non-operational state, that is, the radiation source is preferably switched off. As shown in FIG. 5, in the PET operational state the PET ring 12 has the same imaging field 20 as the CT arrangement in the CT operational state. Thereby, the portion of the subject's body extending into the examination space 16, preferably his/her head or a limb, can be examined by PET and subsequently by CT without requiring the subject to move, the two sets of equipment taking images of substantially the same space part. FIG. 6 is a spatial drawing illustrating the arrangement shown of FIG. 5, showing that the PET ring 12 is inserted between the components of the CT arrangement. It is shown in FIGS. 1 to 6 that the PET ring and the CT arrangement are arranged in a substantially coaxial manner.

Generalising the CT arrangement of the above described embodiment to a second imaging arrangement, according to the embodiment illustrated in FIGS. 1 to 6 in the PET operational state the PET ring 12 is moved into the second imaging arrangement, while in the PET non-operational state it is moved out from the second imaging arrangement.

The embodiment shown in FIGS. 7 to 14 is also explained by way of the example of a CT arrangement. As it is shown also in FIG. 7, in this embodiment the tomographic apparatus 50 comprises as components of the CT arrangement a radiation source 54a, a detector 54b, and a PET ring 52 that are arranged around the examination space 56 in a substantially coaxial manner.

In the embodiment illustrated in FIGS. 7 to 14, the PET ring 52 comprises PET ring portions 52a, 52b that are attached to a support element 54 at one of their sides, the CT arrangement is arranged on the opposite side of the support element 54 with respect to the PET ring 52, and in the PET non-operational state the PET ring portions 52a, 52b are displaced radially outwards along the support element 54 with respect to one another, as illustrated in FIGS. 11 to 14.

Figure 7:
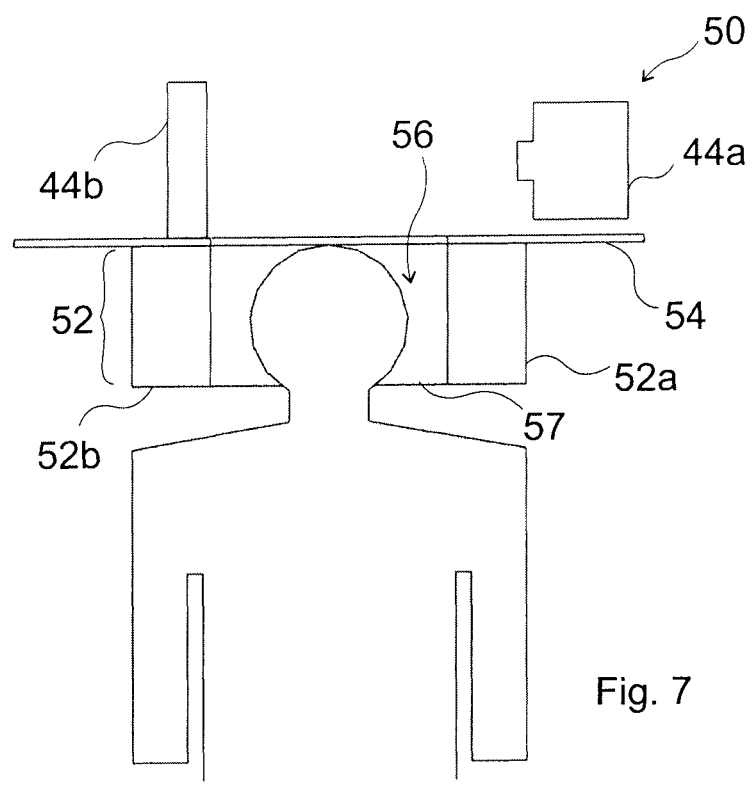
FIG. 7 is a schematic sectional drawing that illustrates a yet further embodiment of the tomographic apparatus according to the invention in the operational state of the PET ring and in the non-operational state of the CT arrangement.
Figure 8:
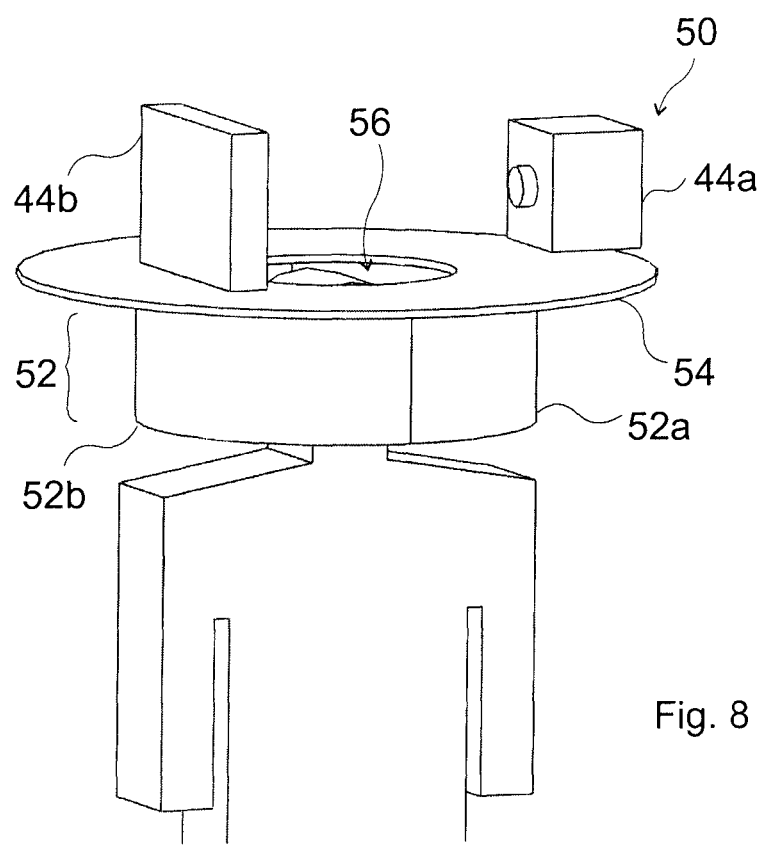
FIG. 8 is a schematic spatial drawing illustrating the state shown in FIG. 7.

In FIG. 7 the PET operational state is illustrated, wherein the ring portions 52a, 52b of the PET ring 52 are assembled, i.e. the ring portions 52a and 52b collectively constitute a ring shape. As it is shown, similar to the above described embodiments, the PET ring 52 is dimensioned such that the subject's head can be comfortably inserted into it; allowing the application of a PET ring having smaller size and better resolution than the whole-body scanners. In FIG. 8 a spatial view of the state illustrated in FIG. 7 is shown, the figure showing also the line dividing the ring portions 52a and 52b.

Figure 9:
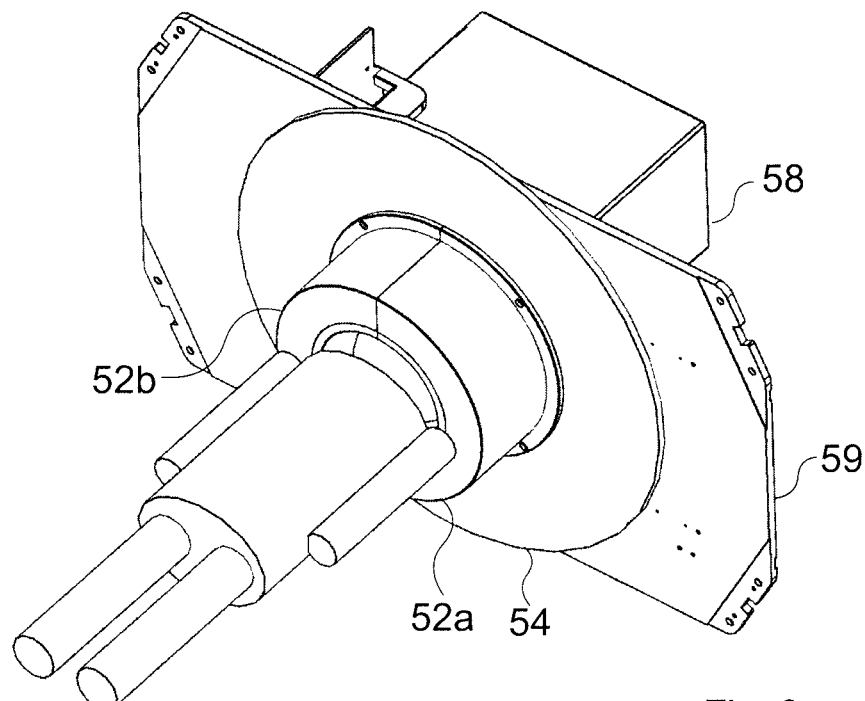
FIG. 9 is another schematic spatial drawing also illustrating the state shown in FIG. 7.
Figure 10:
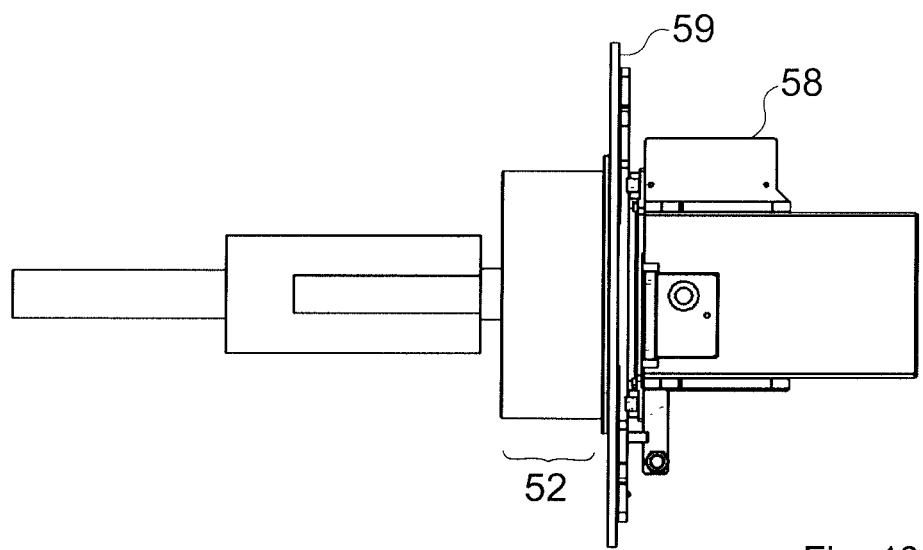
FIG. 10 is a side view of the state shown in FIG. 7.

In FIG. 9 the state shown in FIG. 7 is illustrated in a further spatial drawing. Some of the detector modules of the PET ring 52 can also be observed in this figure. As it is illustrated in FIG. 9, the ring portions 52a and 52b are moved to each other such that they abut against each other. FIG. 9 also illustrates a further structural component 59, to which the support element 54 is attached. FIG. 10 is shows a side view of the state depicted in FIG. 7. In FIGS. 9, 10 a module 58 is shown that comprises the CT arrangement; the module 58 may in certain embodiments comprise an MRI apparatus.

Figure 11:
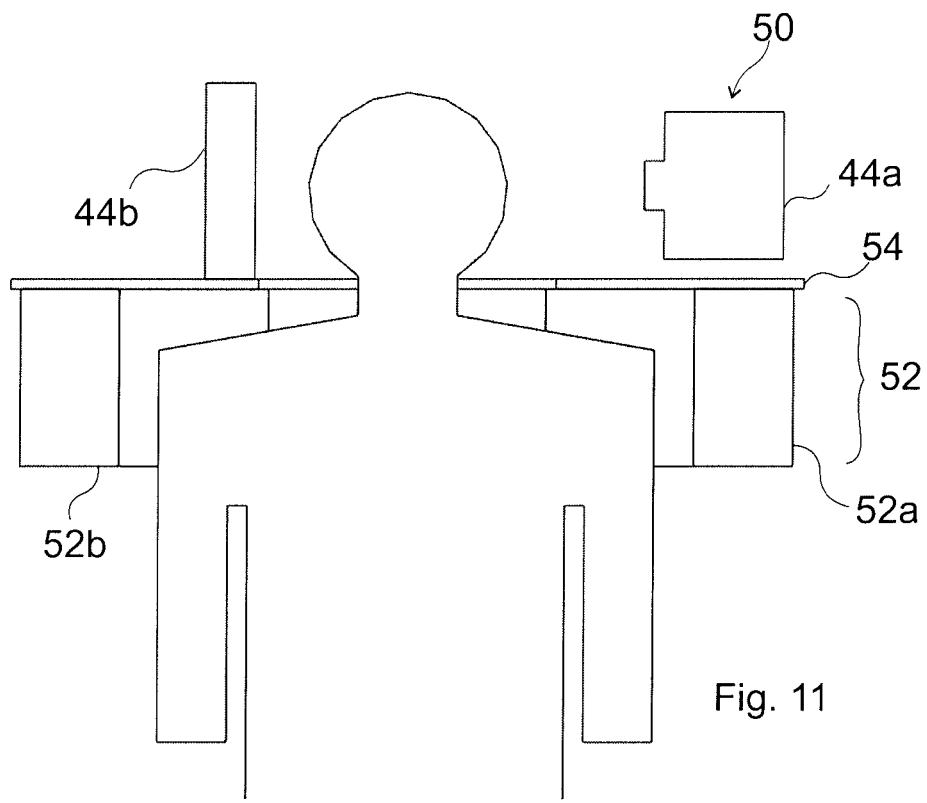
FIG. 11 is a schematic sectional drawing illustrating the embodiment shown in FIG. 7 in the non-operational state of the PET ring and in the operational state of the CT arrangement.
Figure 12:
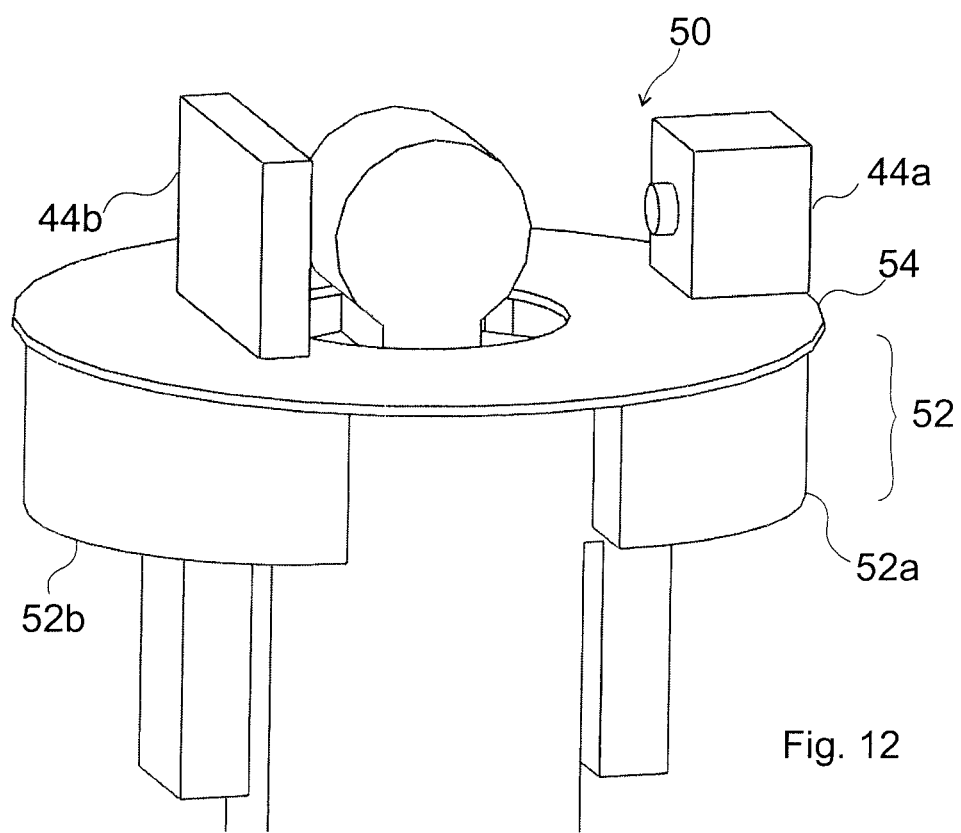
FIG. 12 is a schematic spatial drawing illustrating the state of FIG. 11.

In FIGS. 11 to 14 the CT operational state of the CT arrangement and the PET non-operational state of the PET ring 52 are illustrated. In the PET non-operational state the ring portions 52a, 52b of the PET ring 52 are distanced from each other such that the subject's shoulder can be inserted between them and the head of the subject can be inserted between the radiation source 54a and the detector 54b of the CT arrangement. FIG. 12 is a spatial drawing of the state shown in FIG. 11.

Figure 13:
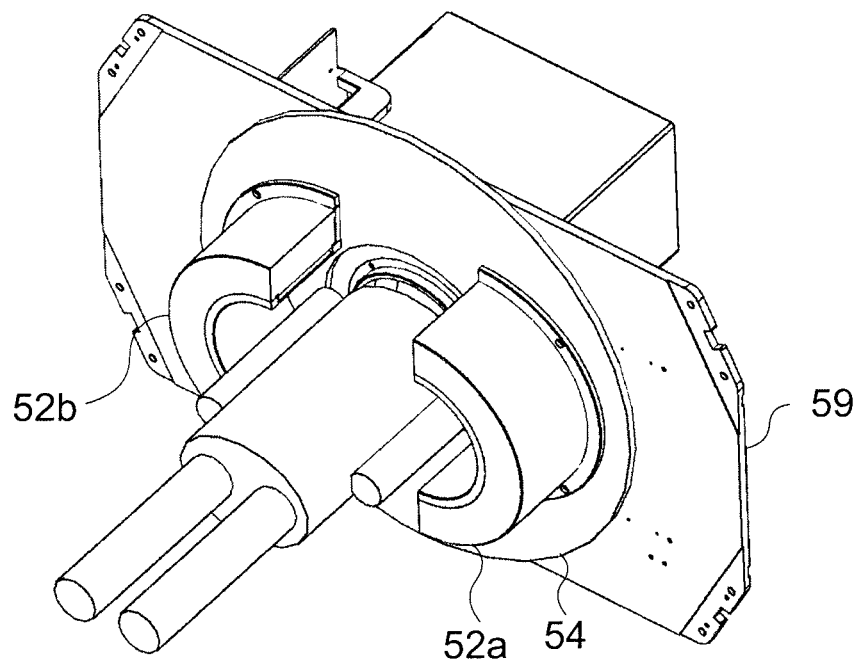
FIG. 13 is a further spatial drawing illustrating the state shown in FIG. 11.
Figure 14:
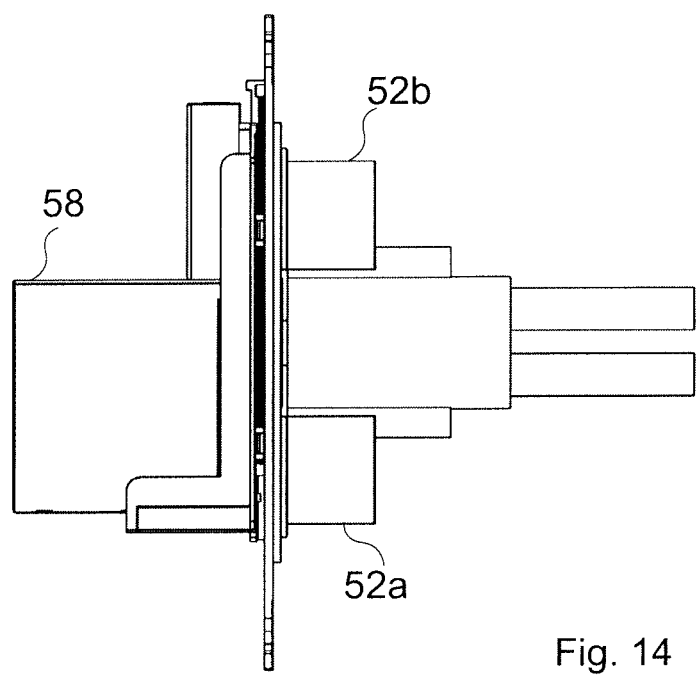
FIG. 14 is a top plan view of the state shown in FIG. 11.

In FIG. 13 the state illustrated in FIG. 11 is shown in an underside spatial view: the opened ring portions 52a, 52b are shown in the figure. The same state is shown in top plan view in FIG. 14.

According to FIGS. 11 to 14, therefore, the PET ring 52 can be brought from the PET operational state to the PET non-operational state by pulling away the ring portions 52a, 52b from each other. Also, in the present embodiment the CT arrangement can be brought from the CT non-operational state to the CT operational state (toggled from one state to other) by way of example in two ways:

after pulling away the ring portions 52a and 52b from each other the apparatus is moved such that the ring portions 52a, 52b encompass the shoulders of the examination subject, and the subject's head gets inserted between the components of the CT arrangement, or
  the examination bed on which the subject lays is moved such that the subject's shoulders enter the suitably large space part created between the ring portions 52a, 52b, and the subject's head gets inserted between the components of the CT arrangement.

In the embodiment illustrated in FIGS. 7 to 14, therefore—generalising the CT arrangement to a second imaging arrangement—, it is the second imaging arrangement that is arranged on the opposite side of the support element 54 with respect to the PET ring 52.

In the tomographic apparatus according to the invention the PET ring preferably has a diameter of 160-340 mm, and is therefore capable of performing brain scans on human subjects. According to the invention the subject's shoulders do not obstruct during the subsequent taking of PET and CT images.

The invention is, of course, not limited to the preferred embodiments described in details above, but further variants, modifications and developments are possible within the scope of protection determined by the claims.

The invention claimed is:

1. A tomographic apparatus for examining a brain or a limb of a human and/or a primate animal, the apparatus comprising:
    an examination space adapted for receiving a subject of a tomographic examination, and
    a PET ring arranged around the examination space in a substantially coaxial manner, wherein the PET ring is displaceable between a PET operational state and a PET non-operational state; and
    a second imaging arrangement arranged around the examination space in a substantially coaxial manner, wherein the second imaging arrangement is adapted for being brought from a second imaging non-operational state to a second imaging operational state in the PET non-operational state of the PET ring, the second imaging arrangement is a CT arrangement having a radiation source and a detector corresponding to the radiation source,
    in the PET operational state the PET ring is moved into between the radiation source, and the detector of the CT arrangement, while in the PET non-operational state, the PET ring is moved out from between the radiation source and the detector of the CT arrangement, and
    in the second imaging operational state, the detector of the CT arrangement is displaced towards the radiation source from the position the detector has in the second imaging non-operational state such that in the second imaging non-operational state the PET ring is allowed to be inserted between the radiation source and the detector of the CT arrangement.

2. The tomographic apparatus of claim 1, wherein the radiation source is arranged such that a side facing an inlet of the examination space of a space part irradiated by the radiation source is aligned substantially parallel with the inlet.

3. The tomographic apparatus of claim 1, wherein the examination space is broadened at an inlet thereof.

* * * * *